United States Patent
Taylor et al.

(10) Patent No.: US 6,236,878 B1
(45) Date of Patent: May 22, 2001

(54) METHOD FOR PREDICTIVE MODELING FOR PLANNING MEDICAL INTERVENTIONS AND SIMULATING PHYSIOLOGICAL CONDITIONS

(76) Inventors: Charles A. Taylor, 2144 Bowdoin St., Palo Alto, CA (US) 94303;
Christopher K. Zarins, 35 Vista Verde Way, Portola Valley, CA (US) 96122;
Thomas J. R. Hughes, 903 Cottrell Way, Stanford, CA (US) 94305

( * ) Notice: Subject to any disclaimer, the term of this patent is extended or adjusted under 35 U.S.C. 154(b) by 0 days.

(21) Appl. No.: 09/083,857

(22) Filed: May 22, 1998

(51) Int. Cl.⁷ ........................................ A61B 5/05
(52) U.S. Cl. .................. 600/416; 600/427; 600/437; 600/439; 606/130; 128/920
(58) Field of Search ................... 600/407, 411, 600/416, 408, 300, 427, 437, 439; 128/920; 606/130

(56) References Cited

U.S. PATENT DOCUMENTS

| | | | | |
|---|---|---|---|---|
| 5,119,816 | * | 6/1992 | Gevins | 128/644 |
| 5,205,289 | * | 4/1993 | Hardy et al. | 128/653.1 |
| 5,682,886 | * | 11/1997 | Delp et al. | 600/407 |
| 5,687,208 | | 11/1997 | Bae et al. | 378/8 |
| 5,687,737 | * | 11/1997 | Branham et al. | 600/523 |
| 5,740,802 | | 4/1998 | Nafis et al. | 128/653.1 |
| 5,947,899 | * | 9/1999 | Winslow et al. | 600/410 |
| 6,026,173 | * | 2/2000 | Svenson et al. | 382/131 |

* cited by examiner

Primary Examiner—Marvin M. Lateef
Assistant Examiner—Jeoyuh Lin
(74) Attorney, Agent, or Firm—Charles A. Taylor (57) ABSTRACT

A method for predictive modeling of human anatomy and physiologic function for planning medical interventions on at least one portion of a body with the goals of improving the outcome of the medical intervention and reducing the risks associated with medical intervention. The method comprising the steps of generation of multi-dimensional continuous geometric models of human anatomy, the generation of models of physiologic functions, the integration of the multi-dimensional continuous geometric human anatomy models with the physiologic functional models, and the use of the integrated models to predict the outcome of medical interventions. Also a method for the integration of multi-dimensional continuous geometric models of human anatomy and models of physiologic function to evaluate and predict changes in physiologic functions in various functional states, stresses and environments and a method for generating data for disease research.

34 Claims, 6 Drawing Sheets

METHOD FOR PREDICTIVE MODELING FOR PLANNING MEDICAL INTERVENTIONS AND SIMULATING PHYSIOLOGICAL CONDITIONS

BACKGROUND OF THE INVENTION

1. Field of the invention

This invention relates generally to computer-assisted modeling and planning systems and in particular to a computer-assisted human anatomic and physiologic modeling system used to predict outcomes of medical intervention and further to predict changes in physiologic function under various states, stresses and environments and still further to generate data for disease research.

2. Discussion of Prior Art

Presently physicians use various types of static images of patient anatomical structures when planning medical intervention including drug therapy, interventions, and surgery. Typically these images are derived from magnetic resonance (MR), computed tomography (CT), angiography, or ultrasound data. In addition, the physician will use tests, such as blood pressure, electrocardiograms (EKGs), and cardiovascular function, taken under at least one physiologic state. Since these images are basically two-dimensional static images, the physician must conceptually construct a multi-dimensional image of the location and shape of existing internal anatomic features within the patient. The physician augments the diagnostic data with empirical clinical information in regards to the anticipated outcome for a given class of medical intervention. The physician, based on this diagnostic and empirical data, may estimate anatomic and physiologic outcome of the medical intervention for a specific patient.

A technique has been developed wherein an interactive surgery planning and display system mixes live video of external surfaces of the patient with interactive computer generated models of internal anatomy obtained from medical diagnostic imaging data of the patient. The computer images and the live video are coordinated and displayed to a physician in real-time during surgery allowing the physician to view internal and external structures and the relation between them simultaneously, and adjust his surgery accordingly. In an alternative embodiment, a normal anatomical model is also displayed as a guide in reconstructive surgery. Another embodiment employs three-dimensional viewing.

Another technique employed in localization of internal structures during surgery is known as stereotactic surgery. With this approach, a rigid mechanical frame is attached to the patient before a CT or MR procedure. The frame and its landmarks can be seen in the resulting images. Mechanisms on the frame, position a probe at specific locations within the image.

In a third technique for localization of internal structures using data from different medical imaging modalities, three-dimensional models of anatomy can be created providing images of selected anatomical features and allowing the visualization of internal structure as solid models.

Another technique may be used for predicting, prior to injection, an organ specific contrast enhancement in a patient for a preselected contrast injection protocol for predetermining a computed tomography scan. The technique uses a computer-generated model of human cardiovascular physiology in a hypothetical patient with a specific body habitus subjected to the pre-selected contrast injection protocol. The predicted contrast enhancement may be then used to control a CT scanner or contrast injector system, to perform the injection and scan with the pre-selected injection protocol and scan parameters. The model includes models of organs and vessels using differential equations to describe mass transport of contrast agent through the cardiovascular system. The technique may also predict optimum injection protocol for contrast agent as well as determining an optimum scan interval when enhancement levels are predicted to exceed a threshold level for a time period greater than the scan duration. Further the technique can be used for monitoring a region of interest in the patient different from the region to be scanned after injection to calibrate the mathematical model and more accurately predict enhancement levels in the tissue to be scanned and calculate the optimum scan parameters.

In all of these techniques, the images and test results are indicators of current patient anatomic features and conditions, but are not indicative of the expected results on patient anatomic features and physiologic function from medical intervention. The physician must conceptualize the integration of the patient's anatomic structure and the physiologic function and must assess the efficacy of the alternatives and then conceptualize the expected results of medical intervention. As medical intervention can range from drug therapy to cardiovascular devices to endovascular stents and bypass grafts considering the alternative interventions and the probable effect on each patient is a monumental task. In addition, the physician must also be able to assess the probable outcome of intervention on all of the patient's physiologic states, stresses and environment.

At present, physicians are expected to be able to predict changes in human physiologic function that will occur after medical intervention, i.e. bypass surgery, solely from the experience base of the past and limited data about the present. Human physiology is far too complex for these predictions to be relevant without more sophisticated analytical and computational tools.

The present invention provides the tools for the physician to rapidly integrate the patient's anatomic data and physiologic function in a single model to predict the outcome of various types of medical interventions and to select the intervention most likely to be successful under a number of different physiologic states, stresses and environments. Further this invention allows the physician and others to predict the impact of various physiologic states, stresses and environments on anatomic structures and physiologic functions of patients. And still further this invention provides for the generation of data useful in disease research.

SUMMARY OF THE INVENTION

The invention is embodied in a method for predictive modeling of human anatomic features and physiologic function for planning medical intervention directed to a portion of a body with the goals of improving the outcome of the medical intervention and reducing the associated risks. This method comprises the generation of a multi-dimensional continuous geometric human anatomy model. A model of physiologic function is then generated and integrated with the anatomic model. Finally, the integrated model is then used to predict the outcome of one or more medical intervention alternatives on a patient. In one embodiment of the invention, the method for predictive modeling is used by the physician and others to plan cardiovascular bypass grafting, and achieve improved outcomes.

In another embodiment of the invention the integrated model is used to evaluate and predict changes in physiologic function in various states, stresses and environments.

A preferred embodiment of the invention is predictive modeling of the outcome of coronary artery intervention procedures, including but not limited to balloon angioplasty, stenting, thrombolysis, atherectomy and coronary bypass grafting.

It is an object of the invention to provide a computer-assisted surgical planning system that predicts patient specific anatomic and physiologic functional outcomes for medical intervention.

Another object of the invention is to provide a computer-assisted surgical planning system for vascular surgery that allows the physician to select the best outcome from various medical interventions and assess the efficacy of design alternatives.

DETAILED DESCRIPTION OF THE INVENTION

The present invention will be described in connection with a system for performing cardiovascular surgery on the cardiovascular system, including the vascular system. However it is not intended to limit the invention to that application. Rather, it is intended to apply to other types of medical intervention planning, device and therapy design and disease research and any other application to which the technology may be beneficially applied. For example, the invention can be applied to other surgeries and to the prediction of outcome of coronary interventional procedures.

Referring now to the detailed drawings there is illustrated a method in accordance with the present invention, which demonstrates the preferred embodiment of the present invention, wherein like referenced numerals refer to like elements throughout the drawings.

Figure 1:
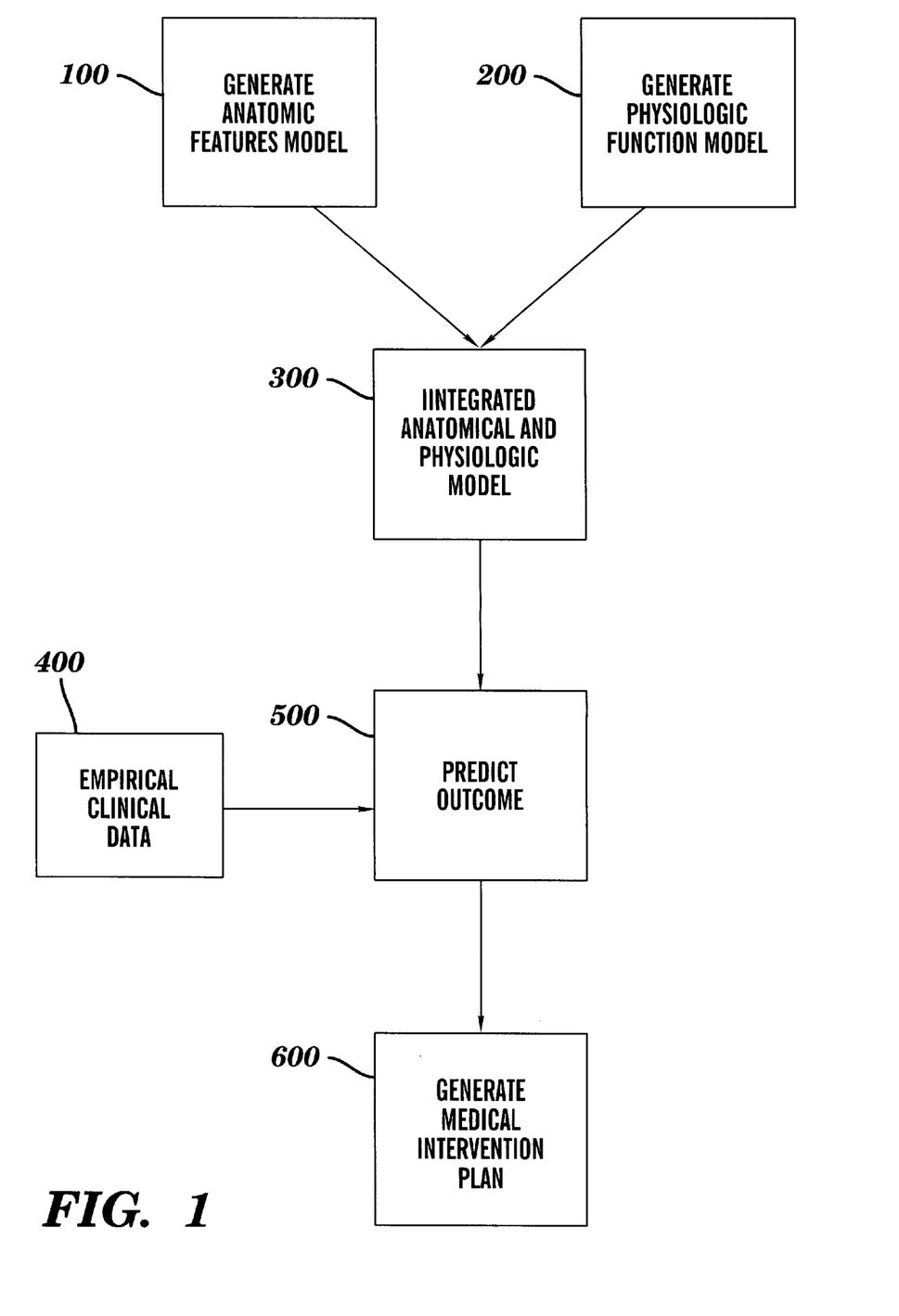
FIG. 1 is a simplified flow chart illustrating the method steps of the present invention used to generate a medical intervention plan.

The main steps in the method for predictive modeling for medical intervention planning are shown in FIG. 1. An anatomical features model 100 is generated. In a parallel or sequential step a physiologic function model 200 is generated. Said anatomical features model 100 is a multi-dimensional continuous geometric anatomy model. Said anatomical features model 100 and said physiologic function model 200 are then combined into an integrated anatomical and physiological model 300. Said integrated anatomical and physiological model 300 is then combined with empirical clinical data 400 to predict at least outcome 500 of medical intervention. Said predicted outcome 500 is then used by physicians and others to generate a medical intervention plan 600.

Figure 2:
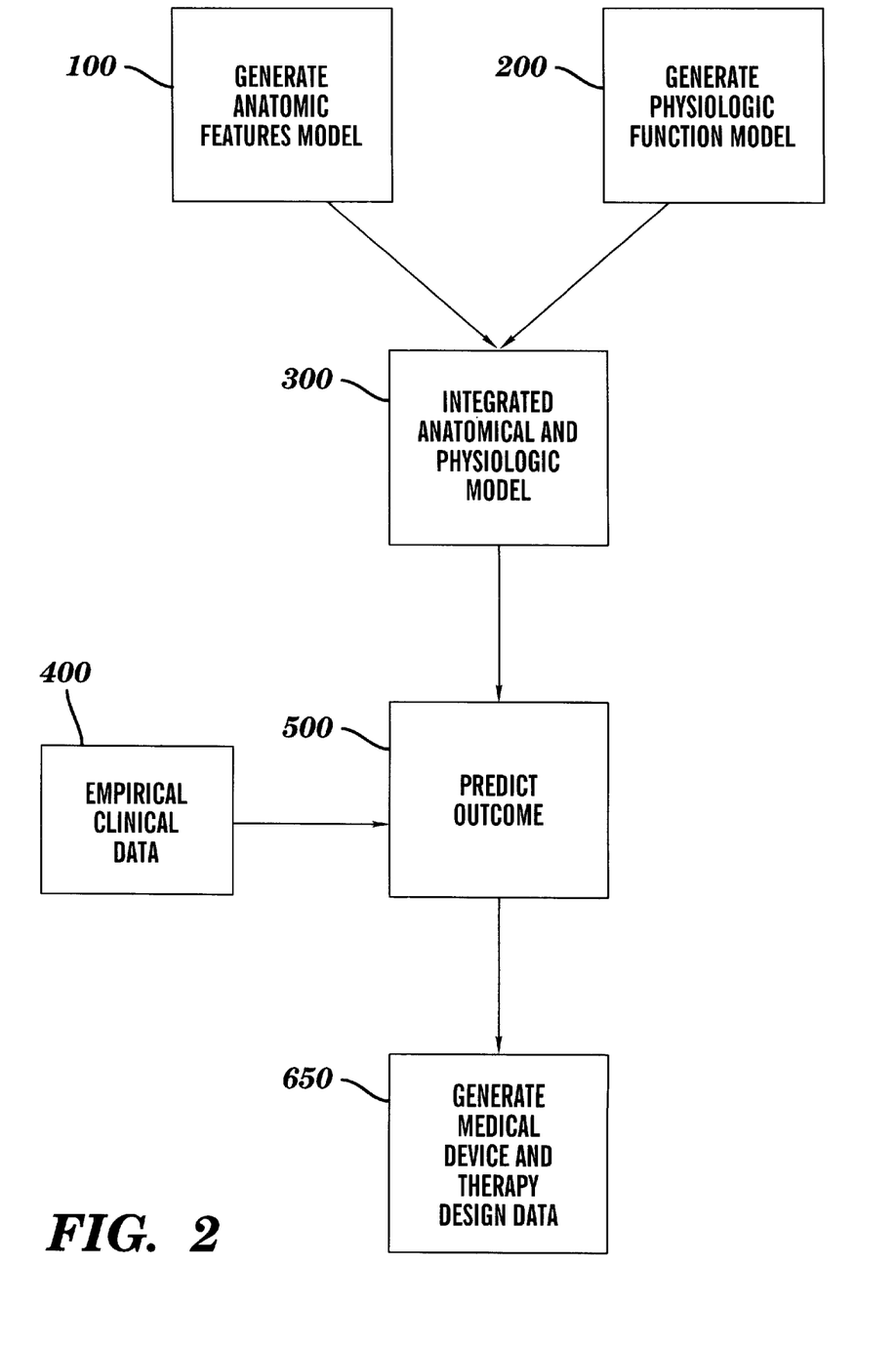
FIG. 2 is a simplified flow chart illustrating the method steps of a second embodiment of the present invention used to generate design data for a medical device or therapy.
Figure 3:
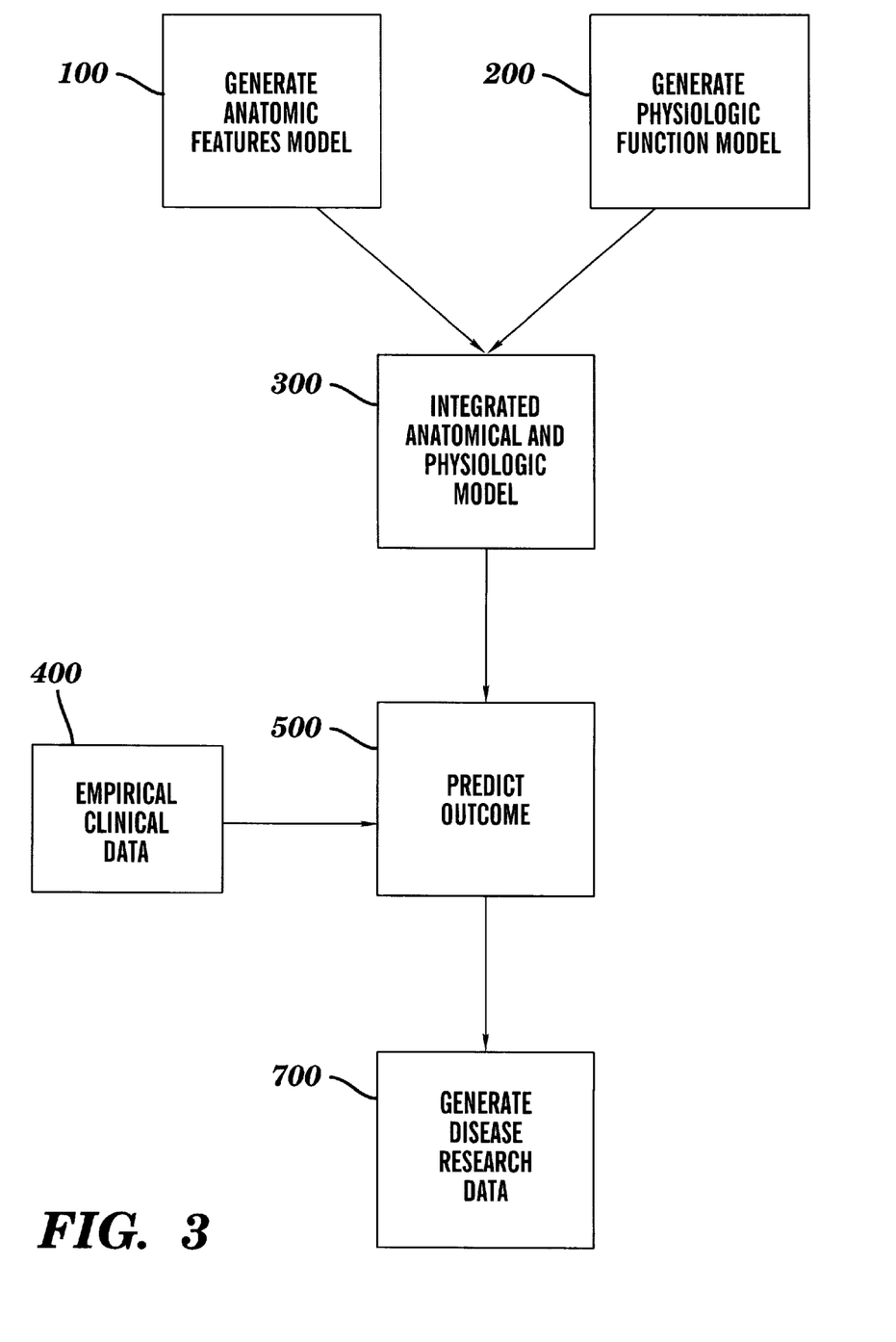
FIG. 3 is a simplified flow chart illustrating the method steps of a third embodiment of the present invention used to generate data for disease research.

The main steps in a second embodiment of the method for predictive modeling is shown in FIG. 2. In this embodiment, the predicted outcome 500 is used by physicians and others to generate data for the design of medical devices or medical therapy 650. In a third embodiment of the present invention, as shown in FIG. 3, the predicted outcome 500 is used by physicians and others to generate data for the disease research 700.

Figure 4:
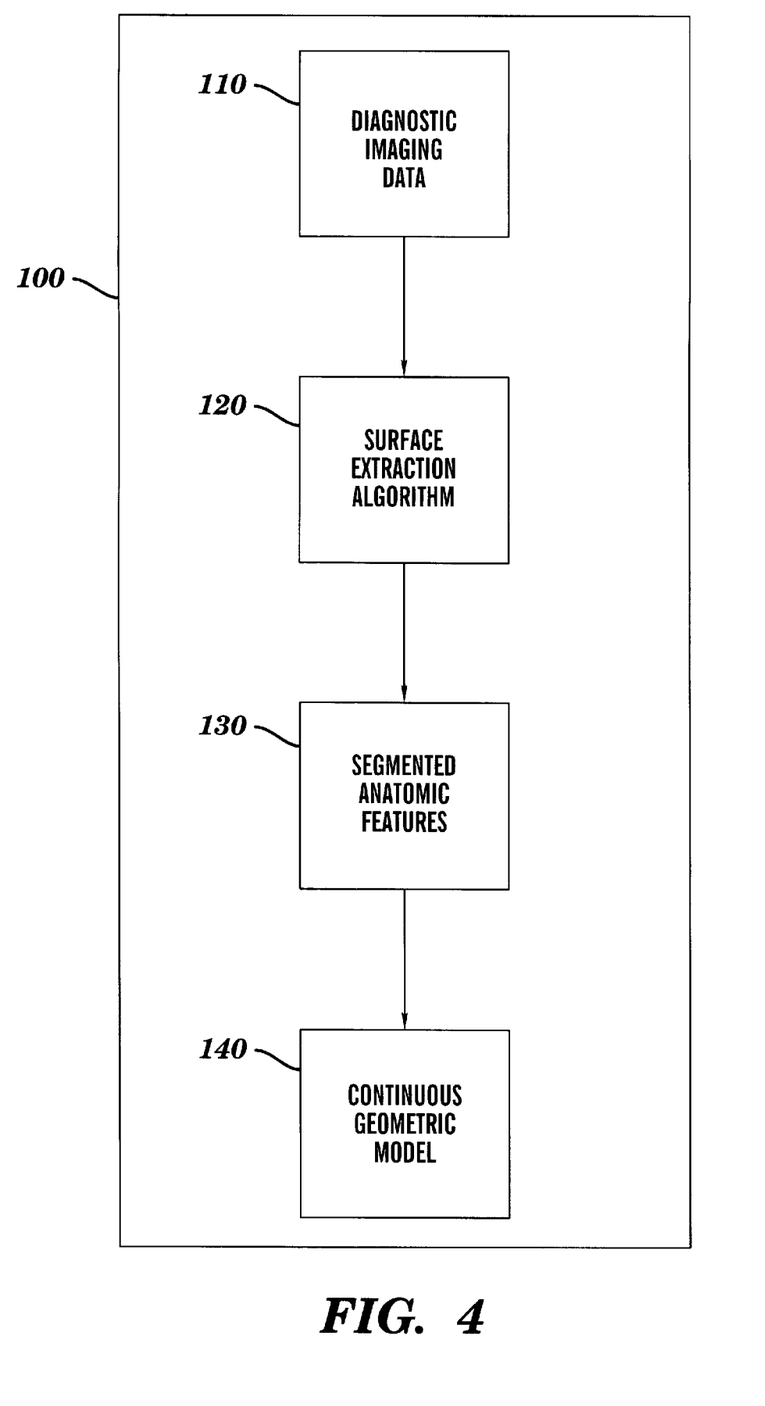
FIG. 4 is a flow chart of a subroutine of the method of FIG. 1, FIG. 2, and FIG. 3 detailing the method steps used to generate a multi-dimensional continuous geometric anatomic features model.

As shown in FIG. 4, said anatomical features model 100 is generated by first collecting diagnostic imaging data 110. The diagnostic data 110 is then mathematically manipulated using a surface extraction algorithm 120 to generate a segmented anatomical features model 130. The segmented features model 130 is then mathematically modified into a continuous geometric model 140, which is then outputted as said anatomical features model 100.

Figure 5:
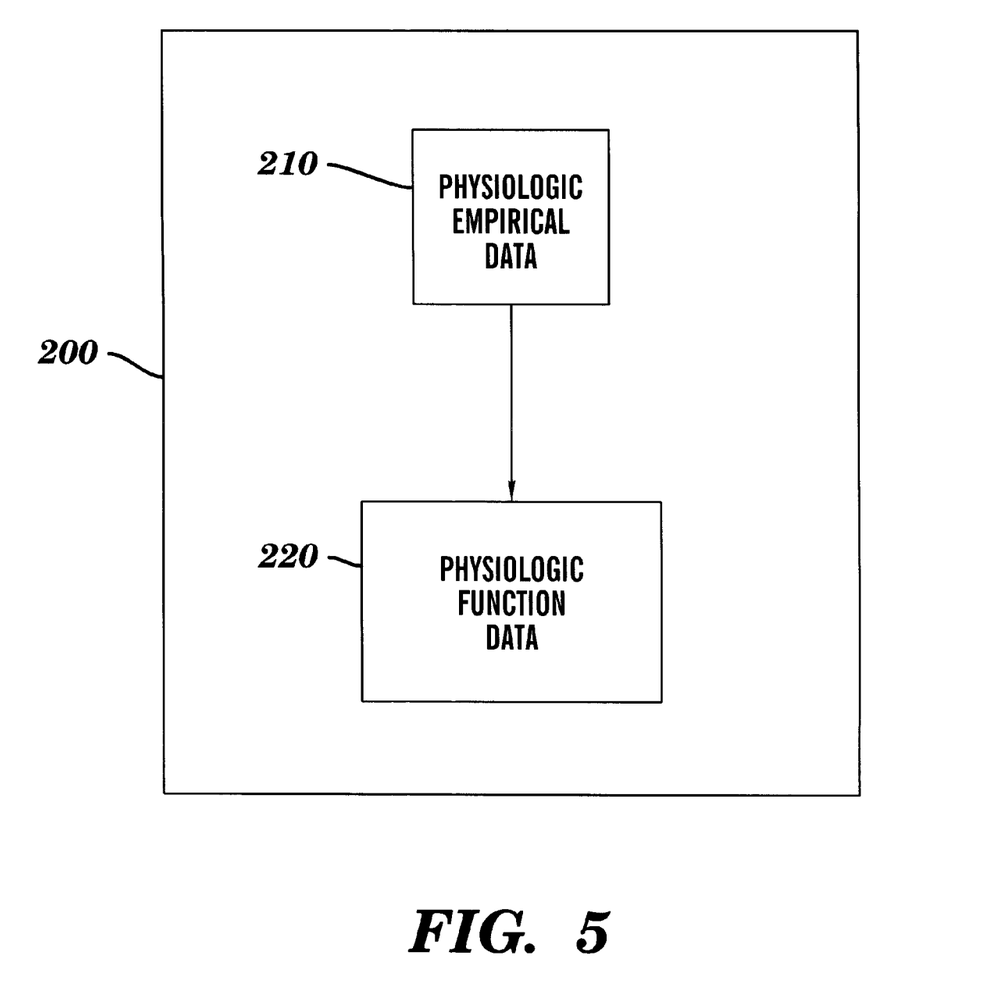
FIG. 5 is a flow chart of a subroutine of the method of FIG. 1, FIG. 2, and FIG. 3 detailing the method steps used to generate a physiologic function model.

FIG. 5 shows the subroutine for the generation of said physiologic function model 200. Physiologic empirical data 210 is added to physiologic functional data 220 to generate said physiologic function model 200.

Figure 6:
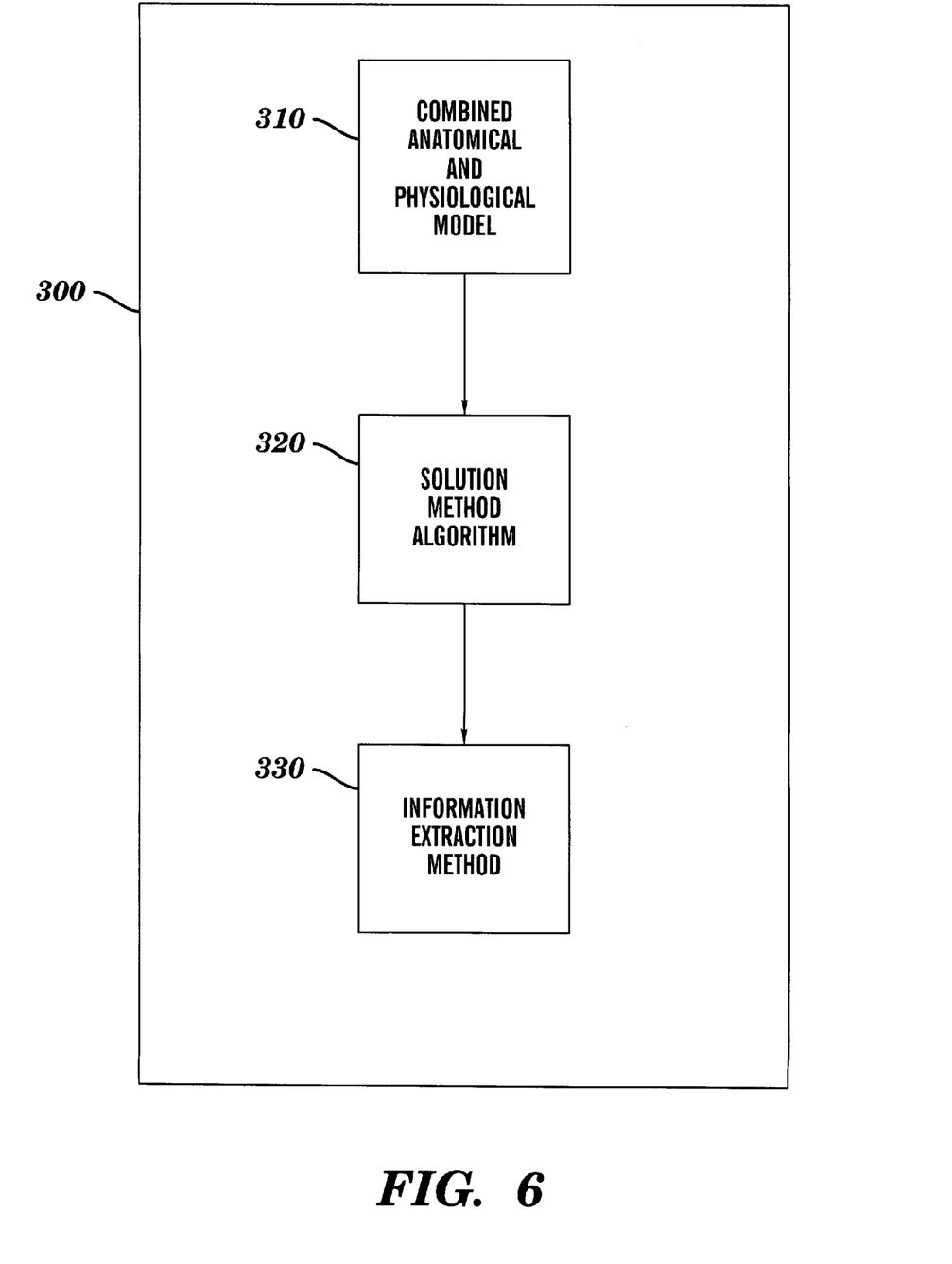
FIG. 6 is a flow chart of a subroutine of the method of FIG. 1, FIG. 2, and FIG. 3 detailing the steps used to generate an integrated anatomical and physiological model.

As shown in FIG. 6, the subroutine for generating said integrated anatomical and physiological model 300 first generates a combined anatomical and physiological model 310. Said combined anatomical and physiological model 310 is then mathematically manipulated using a solution method algorithm 320 and still further manipulated using an information extraction method 330 to produce the integrated anatomical and physiological model 300.

The preferred embodiments of the present invention disclosed herein have been discussed for the purpose of familiarizing the reader with the novel aspects of the invention. Although preferred embodiments of this invention have been shown, many changes, modifications, and substitutions may be made by one having ordinary skill in the art without departing from the scope and spirit of the invention as described in the following claims.

What is claimed is:

1. A method for predictive modeling of human anatomy and physiologic function for planning medical intervention on a portion of a body with the goals of improving the accuracy of the medical intervention and reducing the associated risks, comprising the steps of:

generating a multi-dimensional continuous geometric model of human anatomy having at least one dimension;

generating a model of physiologic function;

integrating the multi-dimensional continuous geometric human anatomy model with the physiologic function model; and predicting the outcome of medical intervention.

2. The method for predictive modeling of claim 1, wherein the generating means for a multi-dimensional continuous geometric model of human anatomy uses a surface extraction algorithm to segment anatomical features.

3. The method for predictive modeling of claim 2, wherein the generating means for a multi-dimensional continuous geometric model of human anatomy uses mathematical methods to describe human anatomy.

4. The method for predictive modeling of claim 1, wherein the multi-dimensional continuous geometric model of human anatomy generating means is computer software.

5. The method for predictive modeling of claim 1, wherein the generating means for a physiologic functional model uses a mathematical algorithm to create said physiologic functional model.

6. The method for predictive modeling of claim 4, wherein a physiologic empirical clinical data is used in the mathematical algorithm used to create said physiologic function model.

7. The method for predictive modeling of claim 5, wherein the generating means for a physiologic functional model uses discrete numerical methods to create (a) said physiologic functional model.

8. The method for predictive modeling of claim 1, wherein the physiologic functional model means is a computer software.

9. The method for predictive modeling of claim 1, wherein the integrating means uses computational mechanics as a solution method algorithm for the integration of the multi-dimensional continuous geometric human anatomy model with the physiologic functional model.

10. The method for predictive modeling of claim 1, wherein the integrating means for the integration of the multi-dimensional continuous geometric human anatomy model with the physiologic function model uses a scientific visualization means as an information extraction method.

11. The method of predictive modeling of claim 10, wherein the scientific visualization means is a computer graphics means.

12. A method for predictive modeling of human anatomy and physiologic function for planning medical intervention on a portion of a body with the goals of improving the accuracy of the medical intervention and reducing the associated risks, comprising the steps of:
   generating a multidimensional continuous geometric model of human anatomy having at least one dimension;
   generating a model of physiologic function;
   integrating the multi dimensional continuous geometric human anatomy model with the physiologic function model; and
   evaluating and predicting the changes in physiological functions in various states, stress and environments in the vascular system.

13. The method for predictive modeling of claim 12, wherein the generating means for a multi-dimensional continuous geometric model of human anatomy uses a surface extraction algorithm to segment anatomical features.

14. The method for predictive modeling of claim 13, wherein the generating means for a multi-dimensional continuous geometric model of human anatomy uses mathematical methods to describe human anatomy.

15. The method for predictive modeling of claim 12, wherein the multi-dimensional continuous geometric model of human anatomy generating means is computer software.

16. The method for predictive modeling of claim 12, wherein the generating means for a physiologic functional model uses a mathematical algorithm to create said physiologic functional model.

17. The method for predictive modeling of claim 16, wherein physiologic empirical clinical data is used in the mathematical algorithm used to create said physiologic function model.

18. The method for predictive modeling of claim 16, wherein the generating means for a physiologic functional model uses discrete numerical methods to create a physiologic functional model.

19. The method for predictive modeling of claim 12, wherein the physiologic functional model means is computer software.

20. The method for predictive modeling of claim 12, wherein the integrating means uses computational mechanics as a solution method algorithm for the integration of the multi-dimensional continuous geometric human anatomy model with the physiologic functional model.

21. The method for predictive modeling of claim 12, wherein the integrating means for the integration of the multi-dimensional continuous geometric human anatomy model with the physiologic function model uses a scientific visualization means as an information extraction method.

22. The method of predictive modeling of claim 21, wherein the scientific visualization means is computer graphics means.

23. A method for predictive modeling of human anatomy and physiologic function for planning medical intervention on a portion of a body with the goals of improving the accuracy of the medical intervention and reducing the associated risks, comprising the steps of:
   generating a multi-dimensional continuous geometric model of human anatomy having at least one dimension;
   generating a model of physiologic function;
   integrating the multi-dimensional continuous geometric human anatomy model with the physiologic function model; and
   generating data for disease research.

24. The method for predictive modeling of claim 23, wherein the generating means for a multi-dimensional continuous geometric model of human anatomy uses a surface extraction algorithm to segment anatomical features.

25. The method for predictive modeling of claim 24, wherein the generating means for a multi-dimensional continuous geometric model of human anatomy uses mathematical methods to describe human anatomy.

26. The method for predictive modeling of claim 23, wherein the multi-dimensional continuous geometric model of human anatomy generating means is computer software.

27. The method for predictive modeling of claim 23, wherein the generating means for a physiologic functional model uses a mathematical algorithm to create said physiologic functional model.

28. The method for predictive modeling of claim 27, wherein physiologic empirical clinical data is used in the mathematical algorithm used to create said physiologic function model.

29. The method for predictive modeling of claim 27, wherein the generating means for a physiologic fictional model uses discrete numerical methods to create (a) said physiologic functional model.

30. The method for predictive modeling of claim 23, wherein the physiologic functional model means is computer software.

31. The method for predictive modeling of claim 23, wherein the integrating means uses computational mechanics as a solution method algorithm for the integration of the multi-dimensional continuous geometric human anatomy model with the physiologic functional model.

32. The method for predictive modeling of claim 23, wherein the integrating means for the integration of the multi-dimensional continuous geometric human anatomy model with the physiologic function model uses a scientific visualization means as an information extraction method.

33. The method of predictive modeling of claim 32, wherein the scientific visualization means is computer graphics means.

34. A method for predictive modeling of human anatomy and physiologic function for planing medical intervention on a portion of a body with the goals of improving the accuracy of the medical intervention and reducing the associated risks, comprising the steps of generating a multi-dimensional continuous geometric model of human anatomy having at least one dimension;

generating a model of physiologic function;

wherein the generating means for said physiologic functional model uses a mathematical algorithm to create said physiologic functional model;

wherein physiologic empirical clinical data is used in said mathematical algorithm used to create said physiologic function model;

integrating the multi-dimensional continuous geometric human anatomy model with the physiologic function model; and evaluating and predicting the changes in physiological functions in various states, stress and environments.

* * * * *